(12) United States Patent
Nichols

(10) Patent No.: US 6,342,049 B1
(45) Date of Patent: Jan. 29, 2002

(54) FEMALE URINE COLLECTION DEVICE

(76) Inventor: Laura L. Nichols, 14826 Bay Oaks Blvd., Houston, TX (US) 77059

( * ) Notice: Subject to any disclaimer, the term of this patent is extended or adjusted under 35 U.S.C. 154(b) by 0 days.

(21) Appl. No.: 09/314,178

(22) Filed: May 18, 1999

Related U.S. Application Data

(63) Continuation-in-part of application No. 08/988,254, filed on Dec. 10, 1997.

(51) Int. Cl.$^7$ .......................... A61F 5/455; A61F 5/451; A61F 5/44
(52) U.S. Cl. ..................... 604/329; 604/327; 604/328; 604/355
(58) Field of Search ................................ 604/327, 328, 604/329, 330, 331, 355

(56) References Cited

U.S. PATENT DOCUMENTS

| | | | |
|---|---|---|---|
| 1,003,821 A | * | 9/1911 | Svejnar |
| 2,157,802 A | * | 5/1939 | Rissinger .................... 128/245 |
| 3,072,125 A | * | 1/1963 | O'Brien ....................... 128/295 |
| 4,198,979 A | * | 4/1980 | Cooney et al. ............. 128/295 |
| 4,563,183 A | * | 1/1986 | Barrodale et al. ........... 604/329 |
| 4,795,449 A | * | 1/1989 | Schneider et al. ........... 604/329 |
| 4,846,818 A | * | 7/1989 | Keldahl et al. .............. 604/329 |
| 4,889,532 A | * | 12/1989 | Metz et al. .................. 604/330 |
| 4,986,823 A | * | 1/1991 | Anderson et al. ............ 604/329 |
| 5,147,301 A | * | 9/1992 | Ruvio .......................... 604/98 |

* cited by examiner

Primary Examiner—John G. Weiss
Assistant Examiner—Michael Bogart
(74) Attorney, Agent, or Firm—Pillsbury Winthrop LLP

(57) ABSTRACT

The female urine collection device includes a formable ring and a collection receptacle. In one embodiment, the receptacle is an external catheter with a flexible neck that passes through and folds back over the ring. In another embodiment, the ring and collection receptacle are integrally formed. In all embodiments, the ring may be placed against the tissue around the urethral meatus to form a seal with the neck, permitting voiding into and through the collection receptacle. The ring may be manually held in place against the tissue around the urethral meatus to form a good seal. A protruding tip or probe may be included and inserted slightly into the vaginal opening or entrance to assure proper placement of the ring. In such embodiments, the ring may be integrally formed with the probe. An adjustable, inflatable pessary anchor may also be provided to help secure the collection receptacle adjacent the genital tissue.

27 Claims, 5 Drawing Sheets

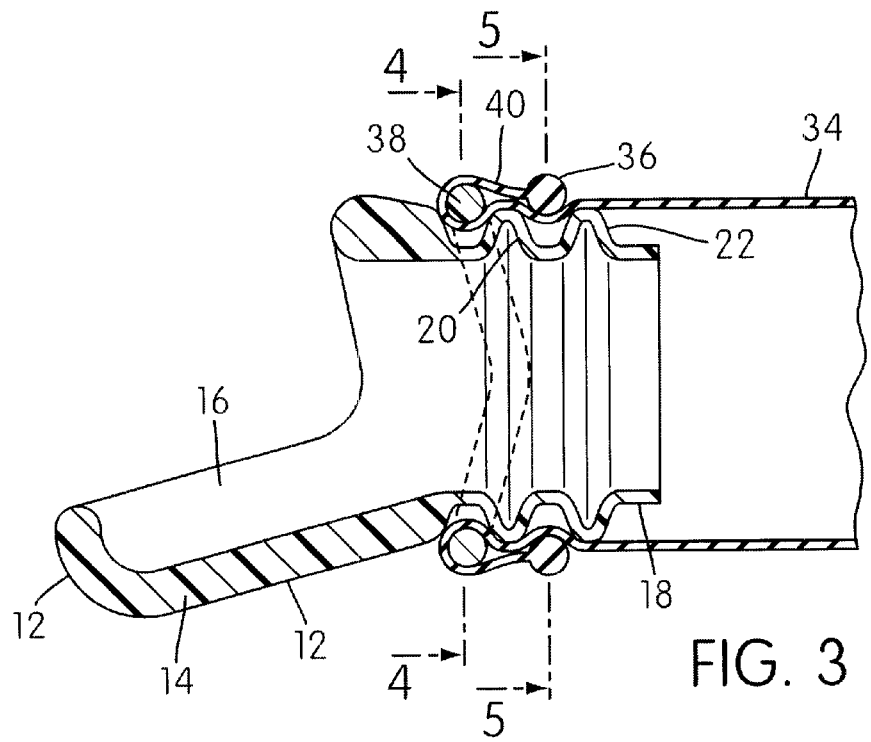
FIG. 3
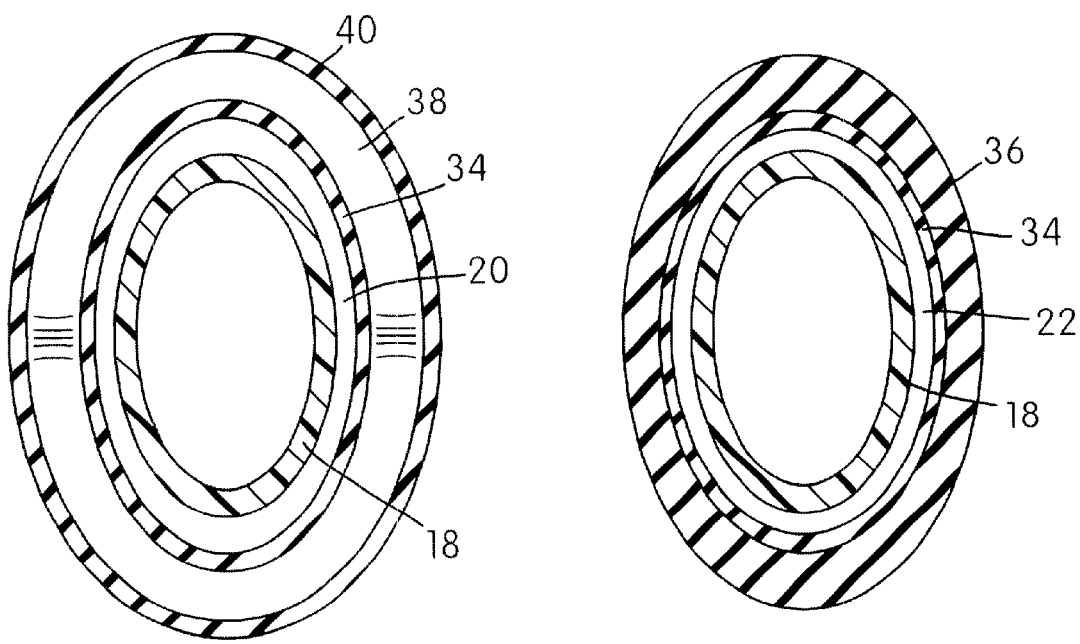
FIG. 4
FIG. 5

FEMALE URINE COLLECTION DEVICE

This is a Continuation in Part of application Ser. No. 08/988,254 filed on Dec. 10, 1997.

BACKGROUND OF THE INVENTION

1. Field of the Invention

The invention is generally related to non-invasive fluid collection apparatus and is specifically directed to a female urine collection device adapted for use in confined environments such as fighter jet cockpits or weightless environments in space and/or for use with invalid or semi-invalid patients.

2. Discussion of the Prior Art

Collection of urine in weightless environments has long been a problem on extended space flights. The problem is particularly complicated for female astronauts. Over the last twenty years, a number of devices have been designed and tested, but to date, all have been rejected because of discomfort in use, leakage and health risks, drawbacks that are particularly unsuitable for extended space flight. In addition, such devices are typically difficult to secure in place, which further aggravates the above mentioned drawbacks. Examples of devices which have proven to be unacceptable are manufactured by Hollister, Inc., Sherwood Medical Company and Rochester Medical. ITW Diamed Division also offered a Misstique External Urinary Collection System at one time. A product sold under the name FemFit has also been tested. The FemFit was rejected because of discomfort. While the Hollister and Misstique devices were more comfortable, they are semipermanent devices which must be fitted internally on the astronaut for the duration of the flight.

More recently, devices have been developed which include a rabbit ear type construction to be inserted into the vagina, with a cup placed over the urinary meatus, to be worn during the entire flight. This prior art device has been found to be undesirable because it is difficult to insert, is often painful to wear, and often leaks due to the collapsible tendency of the cup. In 1989, Merz, et al received U.S. Pat. No. 4,889,532, entitled: FEMALE URINARY INCONTINENCE DEVICE WITH A FORWARDLY-DIRECTED DISCHARGE PASSAGE AND SUPPORT SURFACE PORTIONS. The device is designed to be used primarily while seated, and incorporated a large pad attached to a periurinary meatus cup with a vaginally receptive urine deflective extension. In a weightless environment, the deflective extension actually drives urine into the vagina, causing discomfort, leakage and possible infection. The device is particularly ill-suited for extended space flight use. In a normal gravitational environment, leakage is a serious problem, since fluids tend to collect on the pad and then spill once the pad is removed. However, under weightless conditions, even a slight leak, which may be tolerable in a normal environment, is completely unacceptable. Furthermore, while a number of devices, such as belts and undergarments, have been utilized in attempts to secure these urine collection cups in place, nothing in the prior art has heretofore been found to be acceptable.

Although the above mentioned problems are most acute with respect to space flight, similar problems have been observed in urine collection devices utilized in other environments, such as hospitals or nursing homes, where such devices may be utilized for persons unable to function normally without assistance.

SUMMARY OF THE INVENTION

The subject invention is directed to a urine collection device for use by female astronauts while in a weightless environment. The device is also ideally suited for use in cases where a female patient is confined to a recumbent position. The device of the present invention permits collection of urine, either for disposal or for collection of specimens and samples, without leakage using a non-invasive procedure.

The preferred embodiment of the invention utilizes a malleable ring, preferably of a formable metal or rubber, that can be formed or manipulated to fit by the user or the care provider. A collection receptacle is attached to the ring. In one preferred embodiment, the receptacle is an external catheter and resembles a collapsible bag or cup with an elongated, reduced neck portion secured to the ring. In another embodiment, the receptacle is a cup integrally formed with the ring. In use, the ring is held on the palm side of the hand with the receptacle extending through the gap between the index and forefingers, such that the receptacle and any attached fluid capture bag are located on the back side of the hand. With the bag away from the body, the ring is placed against the tissue around the urethral meatus in a position such that it is in communication with the urinary meatus opening completely surrounding it. The ring is shaped to permit a good fit. The ring is held in position by the two fingers, with the palm of the hand toward and against the genital region and the fingers positioned to point in a posterior direction. The seal is formed by pressing the ring into the tissue around the urinary meatus. This achieves a good seal in the anterior portion of the tissue around the urethral meatus because of the firmness of the tissue in that area. If necessary, a good seal may be assured in the posterior portion of the ring by pressing the lower part of the ring slightly inside the vaginal opening or entrance and against the anterior wall thereof. When properly positioned, the ring should fit between the bones of the pelvis. The user then voids through the ring and into the receptacle which is in fluid communication via a tube with a urine capture device such as a bag or vacuum system. The receptacle may be sealed at the tube by clamping. In some applications, particularly in a weightless environment, the receptacle may be squeezed by the fingers prior to clamping to assure that all of the voided urine is forced into the bag.

Where desired, a probe may be provided on the lower portion of the ring to assure proper positioning of the ring relative to the urinary meatus and the vagina. This is particularly useful when a care giver is using the device with an invalid patient. In one embodiment, such probe may be integrally formed with the ring. In another embodiment, such probe may be integrally formed with the ring and the receptacle.

The device is particularly well suited for use in a weightless environment where gravity cannot be used to assist in the flow of the voided liquid. All of the void is directed into the neck of the receptacle which can be squeezed, as necessary, to assure all of the liquid is driven into a capture bag attached to the device. The device virtually eliminates leakage since it forms a good seal around the urinary meatus opening in a unique and non-invasive manner.

It is, therefore, an object and feature of the invention to provide a convenient, easy to use device for collecting voided liquids in a weightless environment by a female astronaut.

It is also an important object and feature of the invention to provide a urine collection device which may be used by patients while in either a standing, sitting or recumbent position for collection of specimens or for disposal.

It is another object and feature of the invention to provide a female urine collection device that permits collection of the voided liquid in a non-invasive procedure.

It is a further object and feature of the subject invention to provide a urine collection device which is easy to use and may be utilized with minimum training either by the user or by a care giver.

It is an additional object and feature of the invention to provide a female urine collection device that is of simple design and is inexpensive to manufacture, permitting mass manufacture of the units in a disposable configuration.

Other objects and features of the invention will be readily apparent from the drawings and following detailed description.

BRIEF DESCRIPTION OF THE DRAWINGS

FIG. 3 is an enlarged fragmentary sectional view taken generally along line 3—3 of FIG. 1.

FIG. 4 is a cross-sectional view taken along line 4—4 of FIG. 3.

FIG. 5 is a cross-sectional view taken along line 5—5 of FIG. 3.

DETAILED DESCRIPTION OF THE PREFERRED EMBODIMENTS

Figure 8:
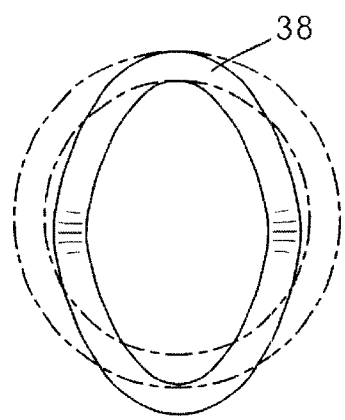
FIG. 8 is a planar view of the malleable ring component of the subject invention, formed to provide a custom fit, with the original ring shape shown in phantom.
Figure 9:
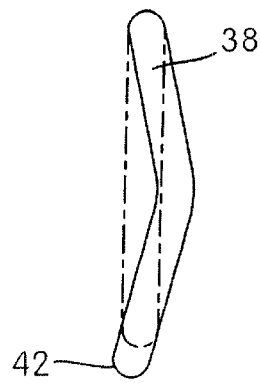
FIG. 9 is an edge view of the ring shown in FIG. 8, also shaped to provide a custom fit, with the original ring shape shown in phantom.

The preferred embodiments of the invention comprise three distinctive configurations that combine a ring with a urine collection receptacle. In one configuration, as shown in FIGS. 1–5, the urine collection device includes a receptacle or periurethral cup 9 having a sleeve 18 and a probe 12 adapted to be placed in the vaginal opening in order to assure proper orientation. This is particularly suited for applications where a care giver is using the device on a patient. Another configuration shown in FIGS. 6 and 7 eliminates the probe and may be used where the probe is not acceptable or desirable. In another configuration shown in the embodiments of FIGS. 10 and 11, the cup is integrally formed with the probe. In any of these configurations, a ring may be used to (i) form a flange or enlarged lip to permit a person to easily and securely hold the urine collection device in place and (ii) form a seal between the device and the tissue around the urethral meatus. The ring may also be used to secure an external catheter to the periurethral cup in configurations incorporating such. FIGS. 8 and 9 illustrate one configuration for the ring.

Figure 1:
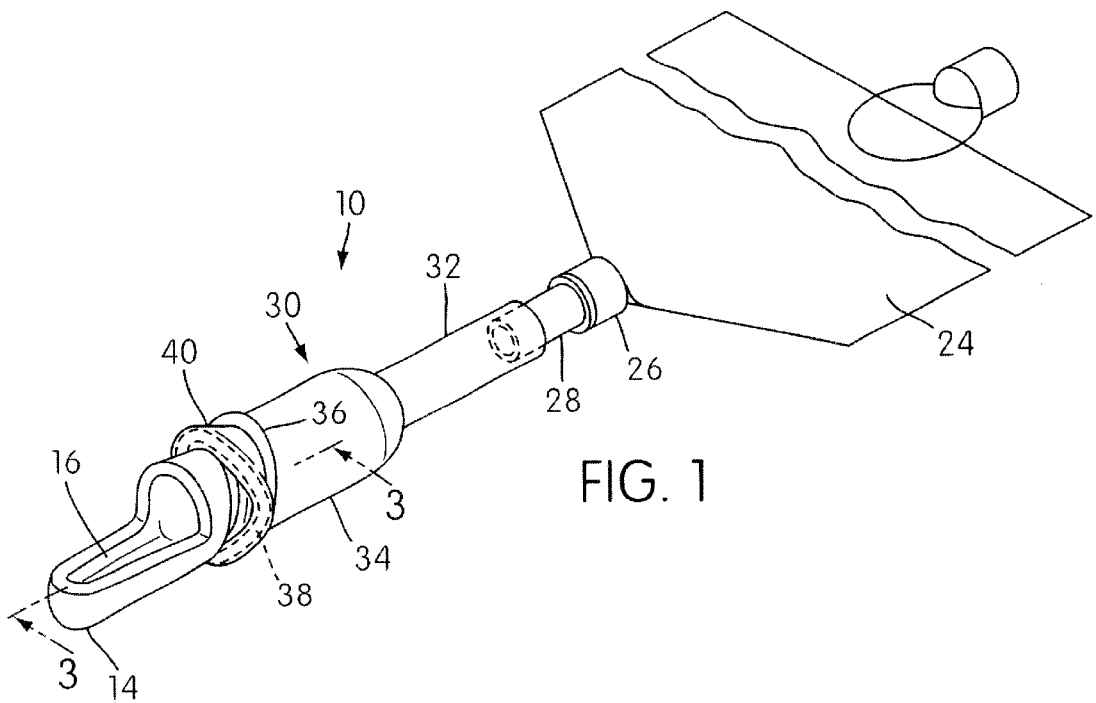
FIG. 1 is a perspective view of the urine collection device of the subject invention.
Figure 2:
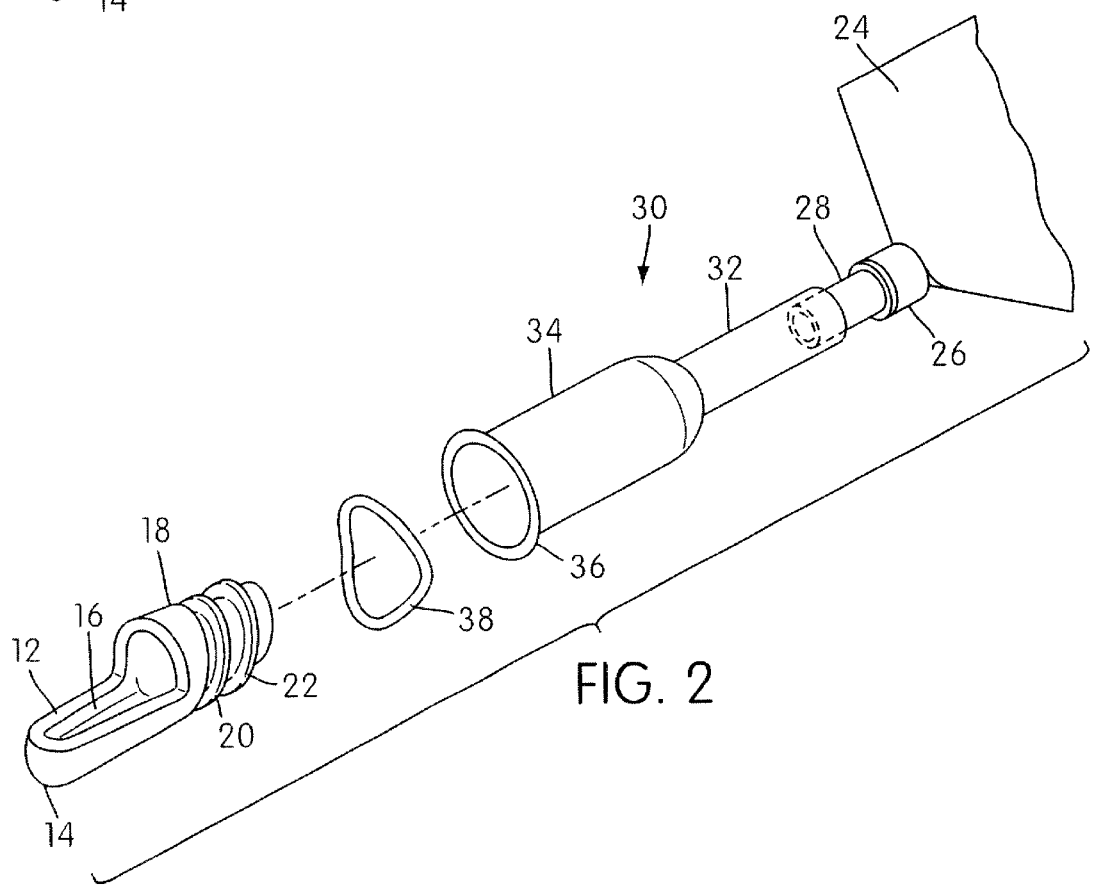
FIG. 2 is an exploded view of the device of FIG. 1.
Figure 10:
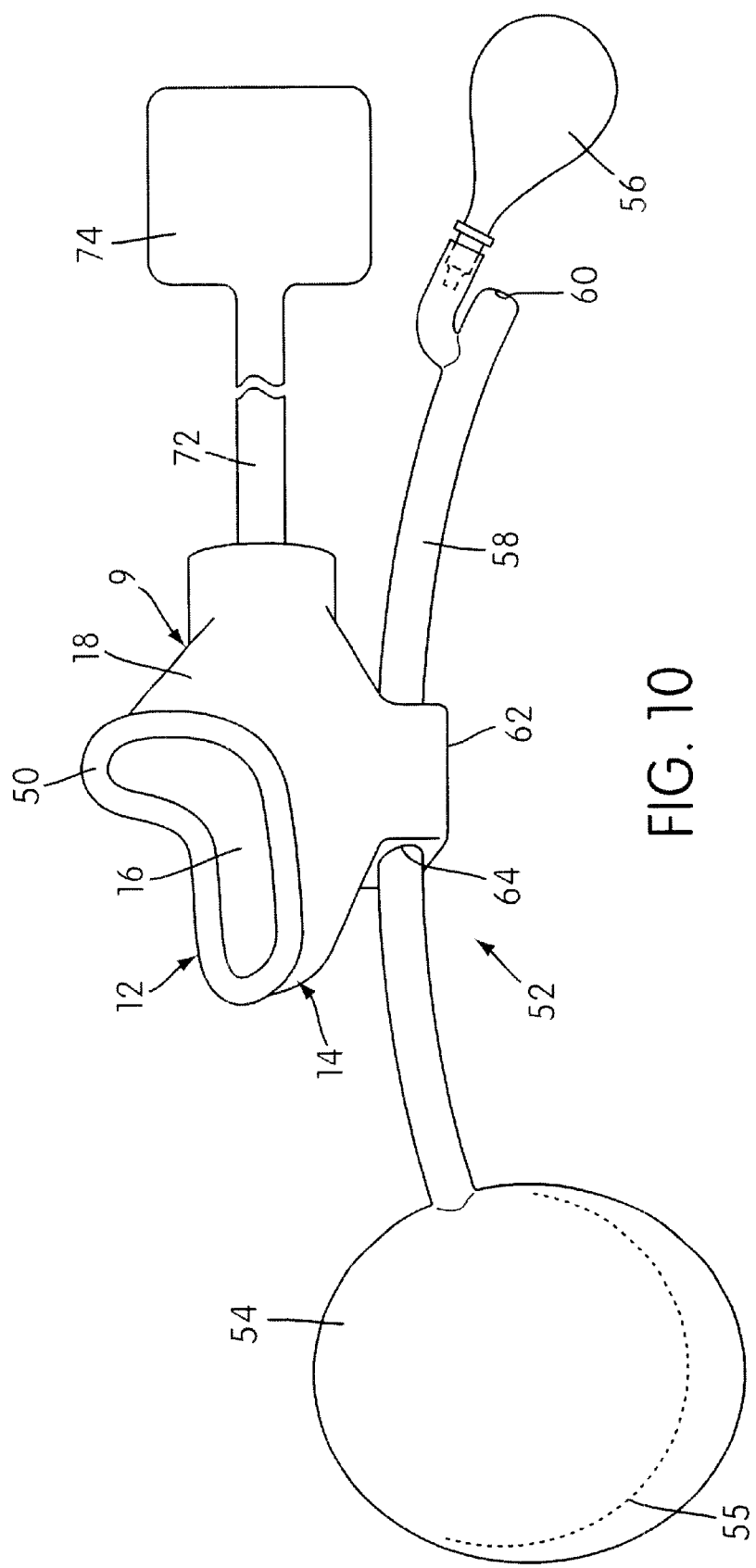
FIG. 10 is a perspective view of an embodiment of the invention in which the ring, receptacle and probe are integrally formed and attached to a pessary anchor.
Figure 11:
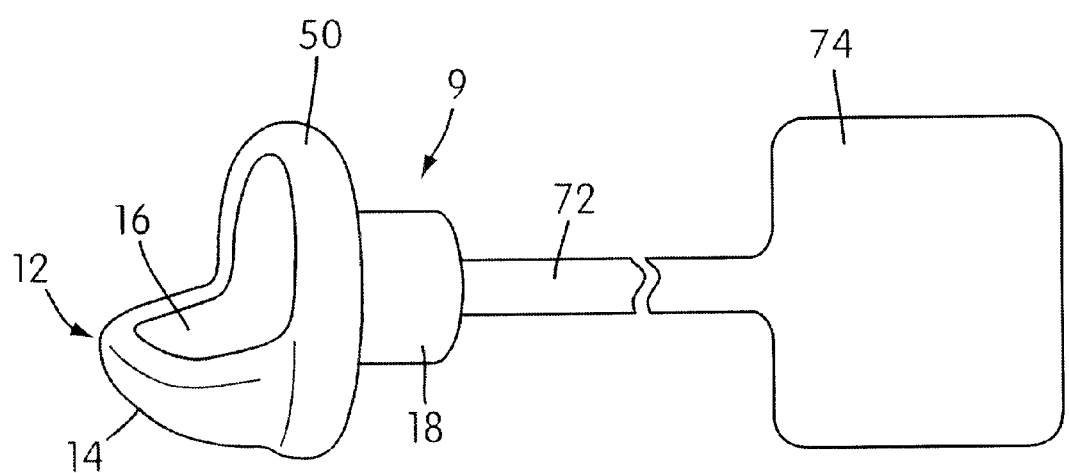
FIG. 11 is a perspective view of another embodiment of the invention in which the ring, receptacle and probe are integrally formed.

With specific reference to FIGS. 1, 2, 10 and 11, the probe component 12 includes a probe end 14 with a radiused tip and formed to define a cupped channel 16. The probe end 14 terminates in an enlarged, generally cylindrical, open ended deformably resilient sleeve 18 around which a ring may be positioned. Depending on the particular configuration and use of ring, the sleeve and probe and ring may be made of unitary construction such as is shown in FIGS. 10 and 11 (see ring 50), or as shown in FIGS. 1 and 2, may be made of assembled discrete components (see ring 38).

Turning to the exemplary embodiment of FIGS. 1 and 2, the sleeve is ribbed as at 20 and 22 to permit the sleeve to seat against the inner surface of the ring. In the illustrated embodiment, the external catheter component comprises a collapsible bag 24, a neck component 30 and a coupler 26 having a reduced portion 28 adapted for receiving a reduced connector end 32 of the neck component 30. The enlarged or expanded portion 34 of the neck component is a tubular member made of a flexible material so that it can be rolled as shown at 36. The outer diameter of the neck 34 is approximately the same as the diameter of the ring 38. When assembling the device, the rolled portion 36 is placed through the ring 38 and folded back over the ring at fold 40 (see FIG. 3). The resilient sleeve can then be compressed or otherwise deformed and inserted into the ring such that the assembled ring and neck are placed over ribs 20 and 22 on sleeve 18, where they are friction held in assembled relationship by the restoration force of sleeve 18 as it presses out against ring 38. When assembled in this manner, ring 38 can serve three functions. First, the diameter of a cross-section of the ring is large enough to function as a flange or lip against which a person can apply pressure to hold the periurethral cup against the tissue around the urethral meatus. Second, having a large diameter also permits the ring to be securely pressed into the soft tissue posterior to the urethral meatus to form a tight seal with the body to the extent the ring is used to form a seal with the body. Third, the ring serves as a rigid surface against which sleeve 18 can press under its radial restoration force to secure and seal the neck component of the external catheter between the ring and the sleeve. More specifically, the sleeve 18 is made of a resilient, slightly flexible material such as, by way of example, a synthetic rubber of the like, and can be formed to fit the shaped ring 38 (see FIGS. 4 and 5). In use, the probe tip 14 is inserted slightly into the vaginal opening to position the opening in the sleeve 18 and the ring 38 in alignment with the urinary meatus opening. The index and forefingers are used to apply axial pressure to the ring such that the ring is held firmly against the tissue around the urethral meatus by the index and forefingers with the neck 32 extending through the fingers and the bag positioned on the back side of the hand.

In this embodiment, while the enlarged portion of the neck is very flexible, the smaller portion will be more firm so that it does not collapse during use. The ribs or ridges on the sleeve are optional and other methods of securing the ring and neck to the assembly may be utilized, as will be known to those who are skilled in the art.

Figure 7:
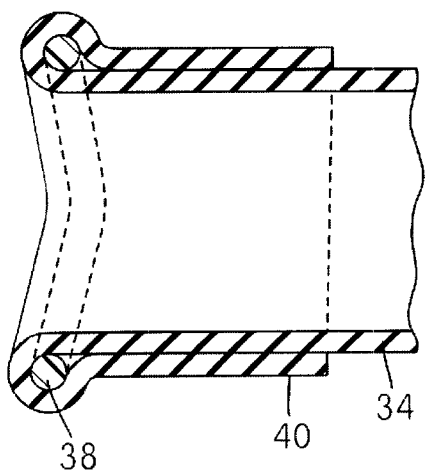
FIG. 7 is an enlarged fragmentary sectional view corresponding generally to FIG. 3 and taken along the line 7—7 of FIG. 6.
Figure 6:
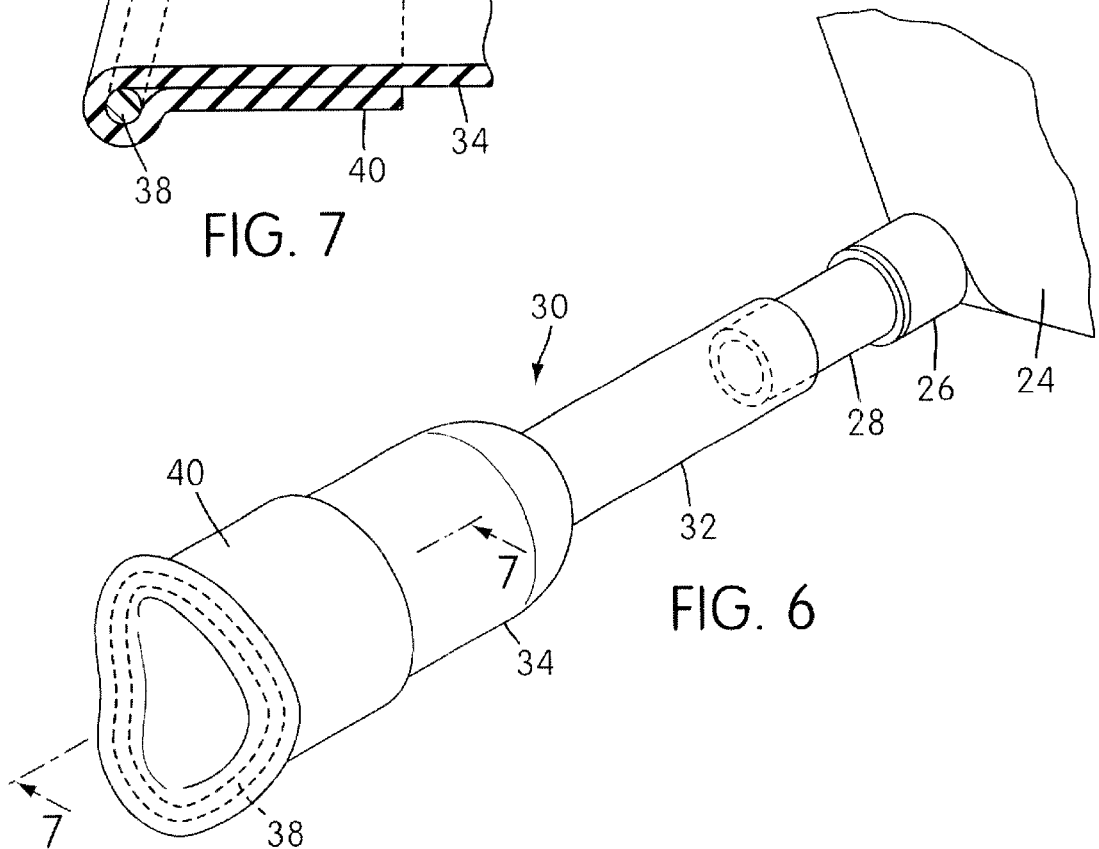
FIG. 6 is a perspective view of the preferred embodiment of the subject invention with the probe device removed.

An embodiment more preferable for use in a weightless environment is shown in FIGS. 6 and 7. As there shown, the bag 24, coupler 26 and reduced portion 28, and the neck assembly 30 are the same as in the embodiment of FIGS. 1–5. The enlarged or expanded portion 34 of the neck is passed through the ring 38 (see FIG. 7) and folded over the ring 38 at fold 40. The outer end of the expanded portion may be rolled as in FIGS. 1–5 or unrolled as in FIGS. 6–7. The length of the fold 40 as shown in FIG. 7 is not a critical part of the invention as long as it is sufficient to eliminate any leakage between the sleeve and the neck. In this second embodiment, ring 38 serves only two functions. First, the diameter of a cross-section of the ring is large enough to function as a flange or lip against which a person can apply pressure to hold the periurethral cup against the tissue around the urethral meatus. Second, this large diameter also permits the ring to be securely pressed into the genital tissue to form a tight seal with the body. In use, the ring is positioned in the palm of the hand, with the neck between the index and forefingers, with the bag on the back side of the hand. The ring is placed firmly against the genital tissue and surrounding the urinary meatus. As better shown in FIGS. 8 and 9, the ring 38 may be formed to provide a good fit, with the posterior end 42 bent slightly toward and, if necessary, slightly into the vaginal opening. The peripheral shape of the ring may be adjusted, as shown in FIG. 8, to fit. It is desirable that the ring fit between the pelvic bones for best results. Again, in this embodiment, while the enlarged portion of the neck is very flexible, the smaller portion will be more firm so that it does not collapse during use.

In the embodiment shown in FIGS. 10 and 11, periurethral cup 9 and probe 12 are integrally formed with a ring 50. Again, probe 12 includes a probe end 14 with a radiused tip and formed to define a cupped channel 16. The probe end 14 terminates in an enlarged, generally cylindrical, open ended deformably resilient sleeve 18 which forms a part of cup 9. In FIG. 10, ring 50 borders the opening formed by the intersection of the open end of sleeve 18 and the open portion of channel 16. In FIG. 11, ring 50 borders the open end of sleeve 18 while probe 12 extends therefrom.

In the embodiment of FIG. 10, periurethral cup 9 is also provided with a pessary anchoring device 52 used to secure cup 9 adjacent the tissue around the urethral meatus. Specifically, anchoring device 50 comprises an inflatable balloon 54 in fluid communication with an air bulb 56 by way of a tube 58. An air bulb 56 may be used to inflate balloon 54. A valve 60 may be provided to control release of air from balloon 54. Of course, those skilled in the art will understand that balloon 54 may have any suitable shape and various methods and structures for inflating and deflating balloon 54 may be used without departing from the invention. In one embodiment, cup 9 is attached to anchoring device 50 by way of an apertured shoulder 62 integrally formed as part of cup 9. Shoulder 62 is provided with an aperture 64 to permit cup 9 to be slidingly mounted on air tube 58. Although not necessary to the general anchoring function of anchoring device 50, balloon 54 may also be provided with one or more drainage apertures 55.

In use, balloon 54 is inserted into the vaginal cavity and inflated until comfortably seated within said cavity. Cup 9 may be slidingly moved along tube 58 until cup 9 is properly positioned against the genital tissue around the urethral meatus. One desirable feature of such an anchor is the ability to adjust the system for different size persons. Specifically, the inflation size of balloon 54 can be adjusted to fit different size vaginal cavities, while the position of cup 9 along flexible tube 58 may be adjusted relative to balloon 54 to accommodate different body shapes and sizes. If balloon 54 is provided with one or more apertures 55, such apertures permit drainage of bodily secretions from the vaginal cavity, such that the anchoring device may be left inserted for extended periods of time without posing infection or other health risks to the user.

In all of the preferred embodiments, the sleeve is preferably formed of a firm but flexible material such as silicone. The neck of the external catheter is preferably formed of a thin, flexible material such as latex. Of course, it will be understood that other materials may be substituted. The ring is preferably a formable material, such as deformable metal for strength or rubber for flexibility. In one embodiment, a deformable metal ring is molded inside of softer rubber, enhancing both the strength of the ring and the ability to seal against the tissue around the urethral meatus. Such an arrangement can be used in any of the above-described embodiments. In integrally formed embodiments, the individual components may be formed of the same material, such as flexible rubber or similar material. Preferably, all materials are inert such that prolonged contact with the user will not cause any type of allergic, infectious, or similar negative reaction by the user.

The neck, sleeve and ring are an assembled device, which may be adapted to be connected to any of a variety of tubes, bags, or other urine capture devices. For example, in FIGS. 10 and 11, tube 72 is provided to attach the invention to a urine collection bag 74. Alternatively, collection bag 74 could be replaced by a vacuum system (not shown) or other fluid/waste collection system. Those skilled in the art will understand that other urine capture devices may be used without departing from the invention.

What is claimed is:

1. A urine collection device for collecting urine from a human female, said urine collection device comprising:

an anchoring device having an anchoring member sized and configured to be inserted into and supported comfortably within the vagina of the human female by means of engagement with the human female's vaginal walls, said anchoring device including an elongated member extending from said anchoring member, said elongated member being configured to extend outside of the vagina when said anchoring member is inserted into and supported within the human female's vaginal cavity; and a urine collection receptacle having a urine-receiving opening configured for surrounding the female's urethral meatus when said device is in use and said urine collection receptacle is positioned against the tissue around the female's urinary meatus;

said urine collection receptacle being slidingly attached to said elongated member to permit the position of said urine collection receptacle on said elongated member to be adjusted relative to said anchoring member by sliding along said elongated member to enhance comfort of, and accommodate the collection of urine from, human females having varying vaginal and urethral sizes, shapes, and relative positions; and said urine collection receptacle having a urine-discharge portion, located generally opposite to said urine-receiving opening, that is configured to have a urine collection container attached thereto;

said urine collection receptacle being configured to direct urine into an attached urine collection container when the female voids urine into said urine collection receptacle through said urine-receiving opening.

2. The urine collection device of claim 1, wherein said anchoring member is expandable.

3. The urine collection device of claim 2, wherein said anchoring member is a balloon.

4. The urine collection device of claim 3, wherein said anchoring device is a pessary and said elongated member is a tube by means of which said balloon is inflated and deflated.

5. The urine collection device of claim 3, wherein said balloon has apertures which are sized to permit drainage of fluid from the female's vaginal cavity when said balloon is positioned therein.

6. The urine collection device of claim 1, wherein said urine collection receptacle comprises a periurethral cup.

7. The urine collection device of claim 6, wherein said periurethral cup is formed from soft, flexible, resilient material such that sides of the periurethral cup can be collapsed together by scissoring between the female's fingers to force voided urine into a urine collection container attached to said periurethral cup.

8. The urine collection device of claim 7, wherein said periurethral cup has a ring surrounding the urine-receiving opening, said ring being of a size and shape to surround the female's urethral meatus and said ring having sufficient rigidity to establish and maintain a seal when manually pressed against tissue around the female's urinary meatus.

9. A urine collection device for collecting urine from a human female, said urine collection device comprising:
   an anchoring device having an anchoring member sized and configured to be inserted into and supported comfortably within the vagina of the human female by means of engagement with the human female's vaginal walls, said anchoring device including a flexible, elongated member extending from said anchoring member, said elongated member being configured to extend outside of the vagina when said anchoring member is inserted into and supported within the human female's vaginal cavity; and
   a urine collection receptacle attached to said flexible, elongated member;
   said urine collection receptacle having a urine-receiving opening that is configured for surrounding the female's urethral meatus when said device is in use and said urine collection receptacle is positioned against the tissue around the female's urinary meatus, said urine collection receptacle being positioned on said flexible, elongated member to bear against the female's genitalia in surrounding relation to the urethral meatus when said anchoring device is inserted into the female's vagina;
   said urine collection receptacle having a urine-discharge portion, located generally opposite to said urine-receiving opening, that is configured to have a urine collection container attached thereto; and
   said urine collection receptacle being configured to direct urine into an attached urine collection container when the female voids urine into said urine collection receptacle through said urine-receiving opening;
   the flexibility of said flexible, elongated member enhancing comfort of, and accommodating the collection of urine from, human females having varying vaginal and urethral sizes, shapes, and relative positions by permitting relative flexible movement between said anchoring member and said urine collection receptacle.

10. The urine collection device of claim 9, wherein said anchoring member is expandable.

11. The urine collection device of claim 10, wherein said anchoring member is a balloon.

12. The urine collection device of claim 11, wherein said anchoring device is a pessary and said elongated member is a tube by means of which said balloon is inflated and deflated.

13. The urine collection device of claim 11, wherein said balloon has apertures which are sized to permit drainage of fluid from the female's vaginal cavity when said balloon is positioned therein.

14. The urine collection device of claim 9, wherein said urine collection receptacle comprises a periurethral cup.

15. The urine collection device of claim 14, wherein said periurethral cup is formed from flexible, resilient material such that the periurethral cup can be collapsed together by scissoring between the female's fingers to force voided urine into a urine collection container attached to said periurethral cup.

16. The urine collection device of claim 15, wherein said periurethral cup has a ring surrounding the urine-receiving opening, said ring being of a size and shape to surround the female's urethral meatus and said ring having sufficient rigidity to establish and maintain a seal when manually pressed against tissue around the female's urinary meatus.

17. A urine collection device for collecting urine from a human female, said urine collection device comprising:
   an anchoring device having an anchoring member sized and configured to be inserted into and supported comfortably within the vagina of the human female by means of engagement with the human female's vaginal walls, said anchoring device including a flexible, elongated member extending from said anchoring member, said flexible, elongated member being configured to extend outside of the vagina when said anchoring member is inserted into and supported within the human female's vaginal cavity; and
   a urine collection receptacle having a urine-receiving opening configured for surrounding the female's urethral meatus when said device is in use and the urine collection receptacle is positioned against the tissue around the female's urethral meatus;
   said urine collection receptacle being slidingly attached to said flexible, elongated member to permit the position of said urine collection receptacle on said flexible, elongated member to be adjusted relative to said anchoring member by sliding along said flexible, elongated member, the slidability of said urine collection receptacle and the flexibility of said elongated member, in combination, enhancing comfort of, and accommodating the collection of urine from, human females having varying vaginal and urethral sizes, shapes, and relative positions by permitting the distance between said urine collection receptacle and said anchoring member to be slidingly adjusted and by permitting relative flexible movement between said anchoring member and said urine collection receptacle; and
   said urine collection receptacle having a urine-discharge portion, located generally opposite to said urine-receiving opening, that is configured to have a urine collection container attached thereto;
   said urine collection receptacle being configured to direct urine into an attached urine collection container when the female voids urine into said urine collection receptacle through said urine-receiving opening.

18. The urine collection device of claim 17, wherein said anchoring member is expandable.

19. The urine collection device of claim 18, wherein said anchoring member is a balloon.

20. The urine collection device of claim 19, wherein said anchoring device is a pessary and said elongated member is a tube by means of which said balloon is inflated and deflated.

21. The urine collection device of claim 19, wherein said balloon has apertures which are sized to permit drainage of fluid from the female's vaginal cavity when said balloon is positioned therein.

22. The urine collection device of claim 17, wherein said urine collection receptacle comprises a periurethral cup.

23. The urine collection device of claim 22, wherein said periurethral cup is formed from soft, flexible, resilient material such that sides of the periurethral cup can be collapsed together by scissoring between the female's fingers to force voided urine into a urine collection container attached to said periurethral cup.

24. The urine collection device of claim 23, wherein said periurethral cup has a ring surrounding the urine-receiving opening, said ring being of a size and shape to surround the female's urethral meatus and said ring having sufficient rigidity to establish and maintain a seal when manually pressed against tissue around the female's urinary meatus.

25. A periurethral cup for collecting urine from a human female, said periurethral cup having a urine-receiving opening which is sized and configured for surrounding the human female's urethral meatus with no or minimal protrusion into just the human female's vaginal opening;

said periurethral cup having a urine-discharge portion, located generally opposite to said urine-receiving opening, that is configured to have a urine collection container connected thereto;

said periurethral cup being formed from soft, flexible, resilient material such that sides of the periurethral cup can be collapsed together by scissoring between the female's fingers to force urine voided into said periurethral cup via said urine-receiving opening into a urine collection container attached to said periurethral cup; and said periurethral cup having a ring surrounding said urine-receiving opening that has sufficient rigidity to establish and maintain a seal when manually pressed against tissue around the female's urinary meatus.

26. The periurethral cup of claim 25, wherein said urine-discharge portion is formed from soft, flexible, resilient material such that said urine-discharge portion of said periurethral cup can be collapsed together by scissoring between the female's fingers.

27. The periurethral cup of claim 25, wherein said periurethral cup has a probe portion that is sized and positioned to extend only slightly into the female's vaginal opening when said periurethral cup is pressed against the tissue around the female's urinary meatus, said probe portion being located on said periurethral cup to facilitate proper positioning of the periurethral cup with the urine-receiving opening surrounding the female's urethral meatus when the probe portion is inserted slightly into the vaginal opening.

* * * * *